United States Patent [19]

Aszalos et al.

[11] Patent Number: 5,650,441

[45] Date of Patent: Jul. 22, 1997

[54] METHOD OF ASSAYING CD4 GLYCOPROTEINS BY USING CERTAIN AZO DYES

[75] Inventors: Adorjan Aszalos, Bethesda; James C. Weaver, Derwood; P. Scott Pine, Rockville, all of Md.

[73] Assignee: The United States of America, as represented by the Secretary of the Department of Health and Human Services, Washington, D.C.

[21] Appl. No.: 320,852

[22] Filed: Oct. 11, 1994

Related U.S. Application Data

[62] Division of Ser. No. 978,144, Nov. 16, 1992, abandoned, which is a continuation of Ser. No. 684,258, Apr. 12, 1991, abandoned.

[51] Int. Cl.⁶ .................................................. A61K 31/17
[52] U.S. Cl. .................................................. 514/397; 514/615
[58] Field of Search .................................. 514/597, 615

[56] References Cited

PUBLICATIONS

Akerfeldt et al J. Med Chem vol. 14(7) 1971 pp. 596–600.
Balzarini et al 104CA:199769b 1986.
Schols et al 110CA:228460a 1989.

*Primary Examiner*—Russell Travers
*Attorney, Agent, or Firm*—Leydig, Voit & Mayer, Ltd.

[57] ABSTRACT

Antiviral compositions useful for the inhibition of HIV include various azo dye compounds which have the ability of inhibiting the binding of HIV rgp120 to CD4 cells on peripheral blood lymphocytes and affecting HIV replication. Also disclosed are methods for treating HIV viral infections with these compositions.

21 Claims, 1 Drawing Sheet

METHOD OF ASSAYING CD4 GLYCOPROTEINS BY USING CERTAIN AZO DYES

This application is a divisional of U.S. patent application Ser. No. 07/978,144, filed Nov. 16, 1992, now abandoned, which, in turn, is a continuation of U.S. patent application Ser. No. 07/684,258, filed Apr. 12, 1991, now abandoned.

BACKGROUND OF THE INVENTION

1. Field of the Invention

The present invention relates to compositions containing azo dye compounds which exhibit antiviral activity and methods for using the same. The azo dye compounds have the ability of inhibiting the binding of HIV rgp120 to CD4 cells on peripheral blood lymphocytes.

2. Description of Related Art

A variety of compounds have been shown to be able to block the binding of HIV to its cellular receptor, CD4. These include soluble CD4 (Smith, D. H. et al, "Blocking of HIV-1 infectivity by a soluble, secreted form of CD4 antigen," *Science* 238 1704–1707 (1987), synthetic fragments of CD4 (Lifson et al, "Synthetic CD4 peptide derivatives that inhibit HIV infection and cytopathicity," *Science* 241 712–716 (1988)). Other anti-HIV compounds include dextran sulfate (Ito et al, "Inhibitory effect of dextran sulfate and heparin on the replication of human immunodeficiency virus (HIV) in vitro," *Antivir. Res.* 7 361–367 (1987)), aurintricarboxylic acid (ATA), Evans Blue (EB) (Balzarini et al, "Aurintricarboxylic acid and Evans Blue represent two different classes of anionic compounds which selectively inhibit the cytopathogenicity of human T-cell lymphotropic virus type III/lymphadenopathy-associated virus," *Biochem. Biophys. Res. Commun.* 136 64–71 (1986a)), and Direct Yellow 50 (Balzarini et al, "Comparative inhibitory effects of suramin and other selected compounds on the infectivity and replication of human T-cell lymphotropic virus (HTLV-III)/lymphadenopathy-associated virus (LAY)," *Int. J. Cancer* 37 451–457 (1986b)). It has also previously been shown that ATA and EB act by binding to CD4 and blocking the binding of HIV rgp120 (Weaver et al, "Polyionic compounds selectively alter availability of CD4 receptors for HIV coat protein rgp120," *AIDS Res. Human Retrovir.* 6 1125–1130 (1990)).

Research has also been conducted concerning compounds with potential antiherpes activity, such as the dye Trypan blue (Alarcon et al, "Screening for new compounds with antiherpes activity," *Antiviral Research*, 4 (1984), pp. 231–243; and Thorne et al, "Inactivation of Measles and Herpes Simplex Viruses by Trypan Blue," *J. gen. Viral.* (1983), 64, pp. 1365–1368), as well as Indigocarmine and Paraorange (Westin et al, "Aromatic Sulfonic Acids as Inhibitors: Structure-Activity Study using Rhino, Adeno 3, Herpes Simplex, and Influenza Viruses," *J. of Med. Chem.*, 1971, Vol. 14, No. 7, pp. 596–600). The dye Congo Red and derivatives thereof have been investigated for potential anti-AIDS activity (Mohan et al, "Potential Anti-AIDS Agents. Synthesis and Antiviral Activity of Naphthalenesulfonic Acid Derivatives against HIV-1 and HIV-2," *J. Med. Chem.*, 1991, 34, pp. 212–217). Also a number of azo dyes were demonstrated to exhibit protective properties in mice infected by equine encephalomyelitis virus (Hurst et al, Brit. J. Pharmacol., 7, p. 455 (1952)).

In view of the above, it remains desirable to discover additional antiviral agents which are effective against the HIV virus.

SUMMARY OF THE INVENTION

Therefore, it is an object of the present invention to provide compositions containing azo dye derivatives which exhibit antiviral activity.

It is also an object of the present invention to provide compositions containing azo dye derivatives which are effective against the human immunodeficiency virus.

It is another object of the present invention to provide a method of treating viral infections of a host in need thereof by administering an antiviral effective amount of an azo dye derivative.

Another object of the present invention is to provide a method for treating the human immunodeficiency virus by administering to a patient an effective amount of a composition containing azo dye derivatives.

It is yet another object of the present invention to provide a diagnostic assay using azo dye compounds.

The foregoing objects and others are accomplished in accordance with the present invention by providing a composition containing certain azo dye derivatives and a pharmaceutically acceptable excipient.

In another embodiment of the present invention, a method is provided for treating viral infections of a host in need thereof by administering an antiviral effective amount of a composition containing certain azo dye derivatives and a pharmaceutically acceptable excipient.

In another embodiment of the present invention, a diagnostic method is provided for assaying CD4 cells by using azo dye compounds.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The invention is further illustrated in the accompanying drawing wherein.

DETAILED DESCRIPTION OF THE INVENTION

Figure 1:
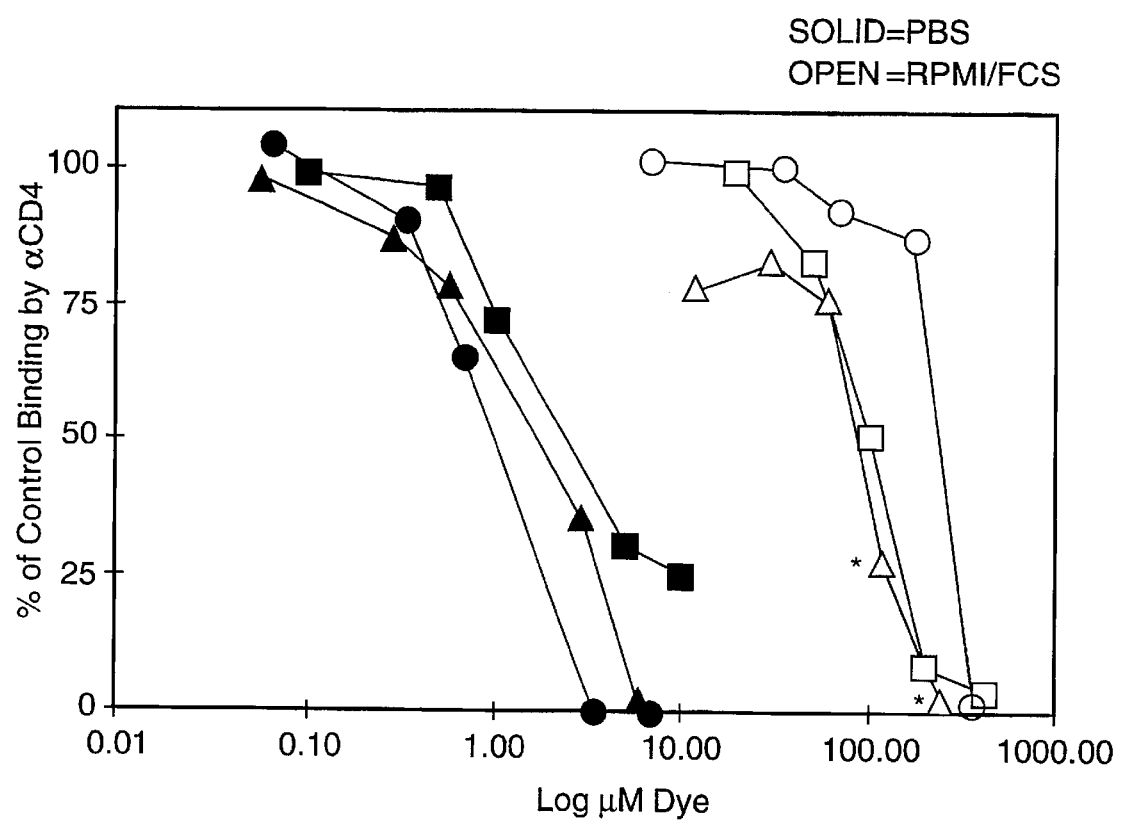
FIG. 1 is a graph showing the dose response of the blocking of binding of αCD4-FITC to CD4 on PBL by the azo dyes.

The azo dye derivatives employed in the present invention generally have the ability of inhibit the binding of HIV rpg120 to CD4 on peripheral blood lymphocytes. These compounds are generally listed in Table A below.

TABLE A

| Cmpd. | Name | Structure |
|---|---|---|
| 1 | FD1 | 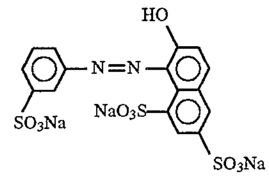 |
| 2 | C.I. Direct Blue 1 | 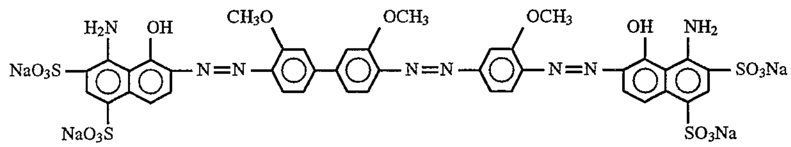 |
| 3 | C.I. Direct Yellow 26 | 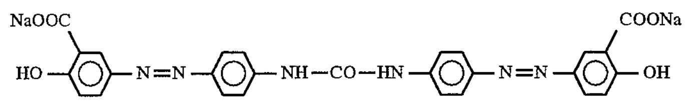 |
| 4 | C.I. Acid Red 89 | 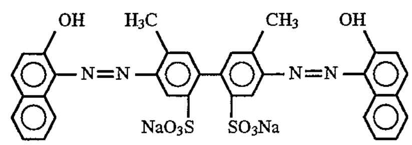 |
| 5 | C.I. Direct Red 75 | 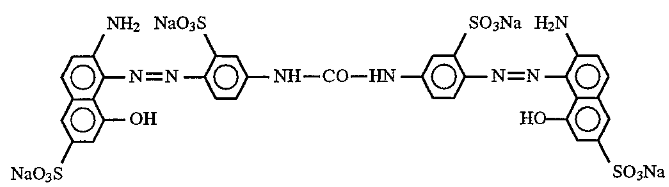 |
| 6 | C.I. Acid Blue 116 | 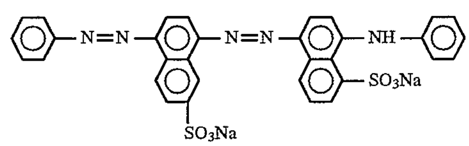 |
| 7 | C.I. Acid Red 115 | 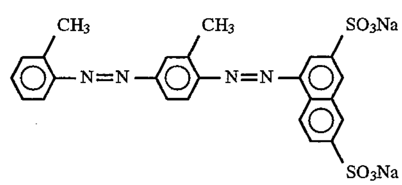 |
| 8 | C.I. Direct Red 79 | 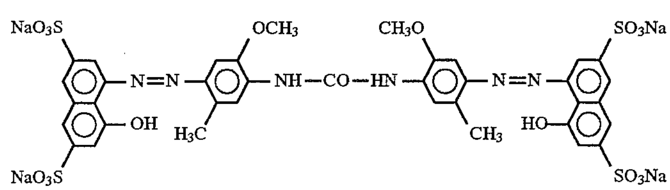 |
| 9 | C.I. Acid Black 3 | 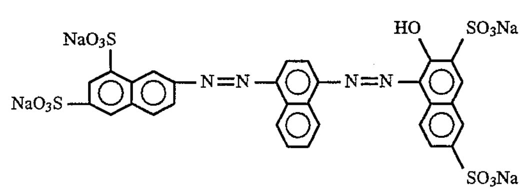 |

TABLE A-continued

| Cmpd. | Name | Structure |
|---|---|---|
| 10 | C.I. Mordant Black 50 | 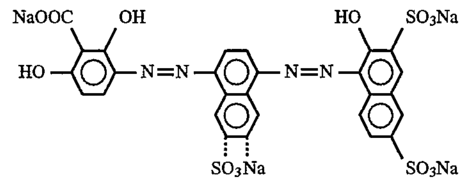 |
| 11 | C.I. Acid Black 36 | 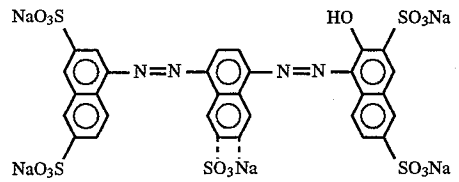 |
| 12 | C.I. Acid Red 47 | 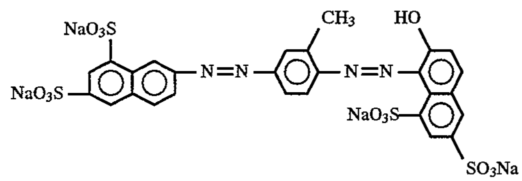 |
| 13 | C.I. Direct Blue 23 | 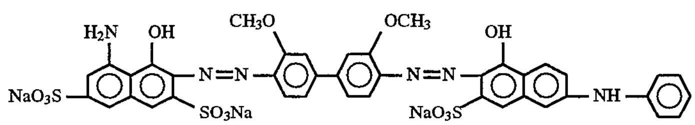 |
| 14 | C.I. Direct Blue 164 | 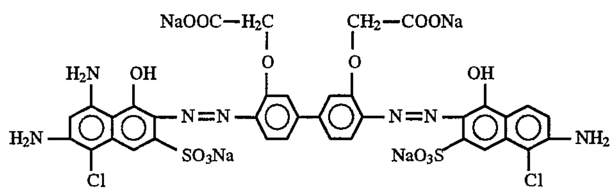 |
| 15 | C.I. Acid Red 170 | 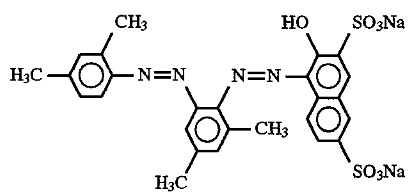 |
| 16 | Acid Dye | 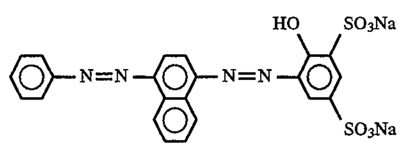 |
| 17 | C.I. Direct Red 85 | 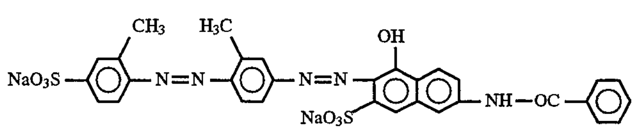 |
| 18 | C.I. Direct Violet 81 | 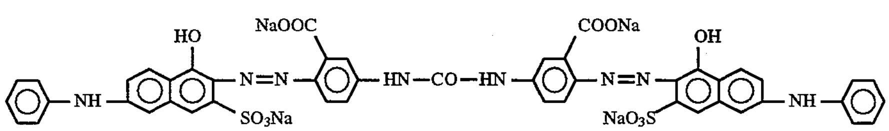 |
| 19 | C.I. Direct Brown 152 | 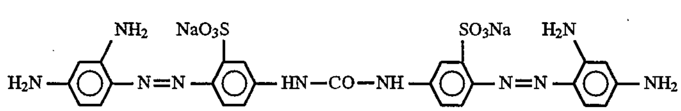 |

TABLE A-continued

| Cmpd. | Name | Structure |
|---|---|---|
| 20 | C.I. Direct Red 49 | (structure) |
| 21 | C.I. Direct Violet 62 | (structure) |
| 22 | C.I. Direct Orange 49 | (structure) |
| 23 | C.I. Direct Orange 69 | (structure) |
| 24 | C.I. Direct Yellow 34 | (structure) |
| 25 | C.I. Direct Brown 126 | (structure) |

Preferred azo dye compounds are Compound Nos. 1–8. Especially preferred azo dye compounds are Compound Nos. 3 and 8. All of the above compounds in Table A are known compounds and are described in Color Index, 3rd ed., vol. 4, Society of Dyers and Colorists, Yorshire BD1-2JB, England (1980) which also discloses further information about how to make or obtain these dye compounds.

The azo dye derivatives of Table A may be employed in accordance with the present invention against various viruses, such as members of the HTLV family including HTLV I, HTLV II, HTLV IV, HTLV V, HIV-1 and HIV-2.

The azo dye compounds of the present invention may also be employed in a diagnostic method for assaying CD4 cells by employing the azo dye compounds employed in the present invention which may bind to the CD4 cells.

The azo dye derivatives employed in the present invention may be made into pharmaceutical compositions by combination with appropriate pharmaceutically acceptable carriers or diluents, and may be formulated into preparations in solid, semi-solid, liquid or gaseous forms such as tablets, capsules, powders, granules ointments, solutions, suppositories, injections, inhalants, and aerosols in the usual ways for their respective route of administration. The following methods and excipients are merely exemplary and are in no way limiting.

In pharmaceutical dosage forms, the azo dye derivatives employed in the present invention may be used in the form of their pharmaceutically acceptable salts, and also may be used alone or in appropriate association, as well as in combination with other pharmaceutically active compounds.

In the case of oral preparations, the azo dye derivatives may be used alone or in combination with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, the azo dye derivatives employed in the present invention may be made into suppositories by mixing with a variety of bases such as emulsifying bases or water-soluble bases.

The azo dye derivatives employed in the present invention may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the azo dye derivatives employed in the invention in the form of a liquid or minute powder may be filled up in an aerosol container with gas or liquid spraying agents, and if desired, together with conventional adjuvants such as humidifying agents. They may also be formulated as pharmaceuticals for non-pressured preparations such as in a nebulizer or an atomizer.

The amount of the azo dye derivatives employed in the present invention to be used varies according to the degree of the infection encountered, and the stages of the disease. A suitable dosage is that which will result in concentration of the azo dye derivative (in blood and/or tissues harboring virus) which are known to inhibit the virus, e.g. about 0.1 to 150 µg/ml, and more preferably about 10–30 µg/ml. The preferred dosage is that amount sufficient to render a host asymptomatic to the particular viral infection.

Unit dosage forms for oral administration such as syrups, elixirs, and suspensions wherein each dosage unit, e.g., teaspoonful, tablespoonful, contains a predetermined amount of the azo dye derivatives employed in the present invention can be by a pharmaceutically acceptable carrier, such as Sterile Water for Injection, USP, or by normal saline.

The azo dye derivatives employed in the present invention can be utilized in aerosol formulation to be administered via inhalation. The azo dye derivatives employed in the present invention can be formulated into pressurized acceptable propellants such as dichlorodifluoromethane, propane, nitrogen and the like.

The term "unit dosage form" as used herein refers to physically discrete units suitable as unitary dosages for human and animal subjects, each unit containing a predetermined quantity of the azo dye derivatives calculated in an amount sufficient to produce the desired effect in association with a pharmaceutically acceptable, diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, for example, vehicles, adjuvants, carriers or diluents are readily available to the public.

Any necessary adjustments in dose can be readily made to meet the severity of the infection and adjusted accordingly by the skilled practitioner.

EXAMPLES

Materials and Methods

Reagents

Evans Blue, aurin tricarboxlyic acid (ATA), and Direct Yellow 50 (Colour Index # 29025) were from Sigma Chemical Co (St. Louis, Mo.). Direct Blue 1 (Colour Index # 24410), Direct Yellow 26 (Colour Index # 25300), Direct Red 75 (Colour Index # 25380), and Acid Blue 116 (Colour Index #26380) were from Matheson Coleman Co (E. Rutherford, N.J.). Acid Red 115 (Colour Index # 27200), Acid Red 89 (Colour Index # 23910), and Direct Red 79 (Colour Index # 29065) were from Sandoz Inc. Monoclonal anti-CD4-FITC (anti-Leu3a) was from Becton Dickinson (Mountain View, Calif.). Recombinant HIV coat protein (rgp120) and monoclonal anti-rgp120-FITC were generous gifts from Genentech Inc, San Francisco, Calif.).

Binding Assays

Human peripheral blood lymphocytes (PBL) were prepared by density gradient centrifugation as previously described (Weaver et al., 1990). The effect of drugs on the binding of anti-CD4-FITC ($\alpha$CD4), anti-CD3-FITC ($\alpha$CD3), anti-CD8-FITC ($\alpha$CDS), or HIV coat protein rgp120 was measured as previously described (Weaver et al., 1990). Briefly, cells were treated with a drug (10' RT) and then FITC labeled antibody or rgp120 followed by anti-rgp120-FITC. Binding was measured by quantitating cell bound fluorescence using flow cytometry. Some binding assays were run in phenol red free RPMI 1640/5% serum instead of the usual PBS to determine effectiveness under cell culture conditions.

Viability Assay

The effect of compounds on the viability of PBL was determined after culturing PBL for 72 hr at 37° C. Some cells were stimulated with 1 µl/ml of anti-T-cell receptor antibody for this time period. Cells were then washed 1× in PBS and resuspended in PBS with 3 µg/ml propidium iodide. After 10 min incubation cells were analyzed by flow cytometry. Live cells were defined as those excluding propidium iodide.

Viral Assays

The effect of various drugs on growth of HIV isolate LAV-1$_{BR}$ in PHA stimulated human PBL was measured using two assays. Reverse transcriptase activity was measured in disrupted virions from the cell free supernatant as previously described (Anand et al, "Interaction between rifabutin and human immunodeficiency virus type-1: inhibition of replication, cytopathic effect and reverse transcriptase in vitro," *Antimicrob. Agents Chemother.* 32 684–688 (1988)). Production of HIV p24 protein was measured from cell lysates using HIV p24 enzyme linked immunosorbent assay kits (Cellular Products, Buffalo, N.Y.) as previously described (Anand et al, "Sodium pentosan polysulfate (PPS), an anti-HIV agent also exhibits synergism with AZT, lymphoproliferative activity and virus enhancement," *AIDS Res. Human Retrovir.* 6 679–689 (1990)).

Results

Inhibition of Binding of $\alpha$CD4 to CD4

Since anti-Leu3a ($\alpha$CD4) and rgp120 bind to the same site on the CD4 molecule, interference in binding of $\alpha$CD4 can be used to screen compounds for possible anti-HIV activity. EB or ATA are used as positive controls since they have been shown previously to block eCD4 and rpg120 binding (Weaver et al, "Polyionic compounds selectively alter availability of CD4 receptors for HIV coat protein rgp120," *AIDS Res. Human Retrovir.* 6 1125–1130 (1990)). Table 1 shows the results of screening the dye compounds listed in Table A for their ability to interfere in binding of $\alpha$CD4 to PBL. Six of the dyes tested show significant ability to block $\alpha$CD4 binding. Three compounds, Acid Blue 116, Acid Red 115, and Direct Red 79 were selected for more complete analysis.

TABLE 1

Some dyes inhibit the binding of αCD4 to PBL

| Compound | Concentration | % Control Binding[1] |
|---|---|---|
| Evans Blue | 1 μM | 1 |
| FD1 | 5 μM | 102 |
| Direct Blue 1 | 10 μM | 1 |
| Acid Red 89 | 7 μM | 6 |
| Direct Yellow 26 | 12 μM | 84 |
| Direct Yellow 50 | 50 μM | 42 |
| Direct Red 75 | 10 μM | 70 |
| Acid Blue 116 | 7 μM | 0 |
| Acid Red 115 | 6 μM | 2 |
| Direct Red 79 | 10 μM | 13 |

[1] Results in % logarithmic mean channel number of αCD4-FITC binding in PBS.

Inhibition of Binding of HIV rgp120 to CD4

The results shown in Table 2 confirm that the three dyes selected on the basis of their interference with αCD4 binding can also block binding of rgp120. Their relative efficacy appears to be similar in both assays.

TABLE 2

Inhibition of HIV rgp120 binding by dyes.

| Compound | Concentration | % Control Binding[1] |
|---|---|---|
| Evans Blue | 1 μM | 8 |
| Acid Blue 116 | 7 μM | 9 |
| Acid Red 115 | 6 μM | 10 |
| Direct Red 79 | 10 μM | 30 |

[1] Results in % logarithmic mean channel number of rgp120 binding detected by binding of αrpg120-FITC in PBS.

Specificity of Inhibition of Binding

We have analyzed the specificity of these compounds by testing their ability to interfere with the binding of two other monoclonal antibodies, αCD3 and αCD8. The results in Table 3 show that Acid Blue 116 reduces binding of both antibodies by about ½, Acid Red 116 interferes with αCD3 but not αCD8, and Direct Red 79 does not affect binding of either antibody. The increase in binding of αCD3 on Direct Red 79 treated cells may reflect nonspecific binding.

TABLE 3

Specificity of inhibition of binding of monoclonal antibodies by dyes.

| Compound | Concentration | % Control Binding[1] αCD4 | αCD3 | αCD8 |
|---|---|---|---|---|
| Evans Blue | 1 μM | 1 | — | — |
| Acid Blue 116 | 4 μM | 1 | 44 | 54 |
| Acid Red 115 | 6 μM | 2 | 41 | 90 |
| Direct Red 79 | 20 μM | 22 | 124 | 106 |

[1] Results in % logarithmic mean channel number of αCD4-FITC, αCD3-FITC, or αCD8-FITC binding in PBS.

Dose Response of Inhibition

FIG. 1 shows the dose response curves for the three dyes. The solid symbols are for incubation in PBS and the open are for incubation in complete cell culture medium (RPMI 1640 w/5% serum). Circles are Acid Blue 116; Triangles are Acid Red 115; and Squares are Direct Red 79. In the presence of serum about 100× more dye is needed for efficacy, this may be due to the dyes binding to serum proteins. For Acid Blue 116 and Acid Red 115, these concentrations are near their limits of solubility in aqueous solutions.

Effect of Compounds on Viability

On the basis of specificity and dose response in serum containing medium Direct Red 79 was selected for further testing. First the effect of this dye on cell viability was tested. Table 4 shows that Direct Red 79 has no effect on the viability of PBL after 72 hr of continuous culture. ATA was used as a positive control since it does not bind to serum proteins (not shown). Table 5 shows that Direct Red 79 has a limited effect on the proliferation of αTCR stimulated PBL.

TABLE 4

Effect of Direct Red 79 on viability of PBL after 72 hr culture.

| Treatment | Concentration | % Viable Cells[1] |
|---|---|---|
| None | — | 90 |
| ATA | 10 μM | 86 |
| Direct Red 79 | 400 μM | 89 |

[1] Viability determined by ability to exclude propidium iodide as measured by flow cytometry.

TABLE 5

Effect of dyes on viability of PBL after 72 hr culture of anti-TCR stimulation.

| Treatment | Concentration | % Viable Cells[1] |
|---|---|---|
| None | — | 78 |
| Direct Red 79 | 100 μM | 54 |

[1] Viability determined by ability to exclude propidium iodide as measured by flow cytometry.

Effect of Compounds on HIV Replication in vitro

We tested the ability of Direct Red 79 to affect HIV replication in vitro using two assays. First we determined that the compound is able to strongly inhibit the production of reverse transcriptase activity after six days of culture (Table 6). Next, to eliminate the possibility that the dye was directly inhibiting the RT we measured the amount of intracellular HIV p24 protein. Table 7 shows that the dye is able to strongly decrease p24 production.

TABLE 6

The effect of Direct Red 79 on HIV reverse transcriptase activity after six day culture.

| Treatment Count | CPM RT[1] | % Inhibition | No. Cells |
|---|---|---|---|
| Cells only | 76 | — | — |
| HIV only | 2026 | — | — |
| DMSO | 6338 | 0 | 2.00 × 10⁶/ml |
| ATA (1 μM) | 109 | 97 | 0.15 × 10⁶/ml |
| Direct Red 79 (100 μM) | 145 | 97 | 1.89 × 10⁶/ml |

[1] Counts per minute [³H]-TTP incorporated into TCA precipitable material by reverse transcriptase after two hours incubation.

TABLE 7

The effect of Direct Red 79 on production of intracellular HIV p24 as measured by ELISA.

| Treatment | pg/ml HIV p24 |
|---|---|
| Cells only | 0 |
| Virus only | 2556 |
| DMSO | 1222 |

TABLE 7-continued

The effect of Direct Red 79 on production of intracellular HIV p24 as measured by ELISA.

| Treatment | pg/ml HIV p24 |
|---|---|
| ATA (2.5 μg/ml) | 0 |
| ATA (0.25 μg/ml) | 111 |
| Direct Red 79 (5 μg/ml) | 333 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method of detecting the presence or absence of CD4 glycoprotein in a sample, which method comprises contacting said sample in vitro with an azo dye derivative selected from the group consisting of

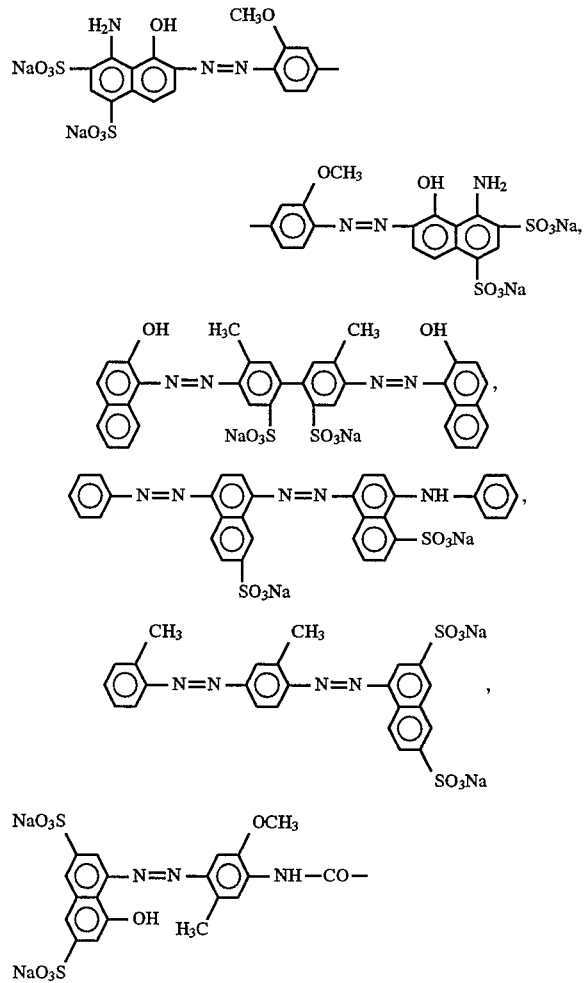

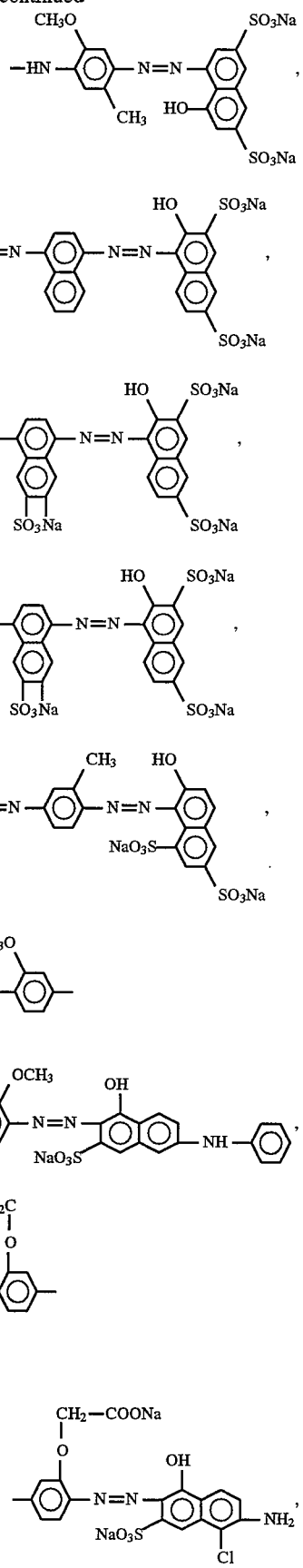

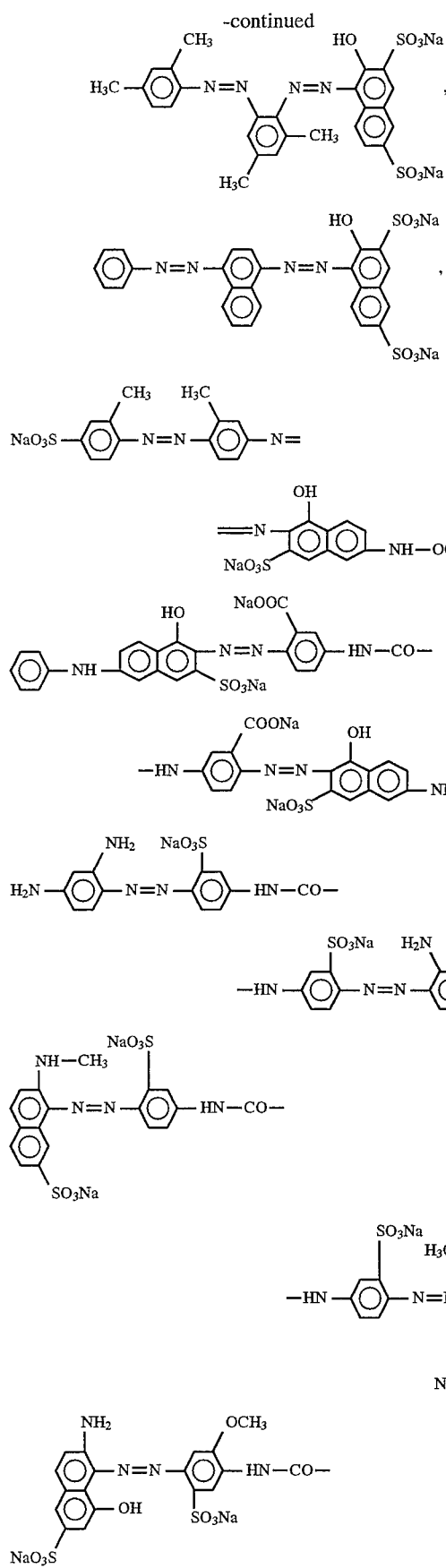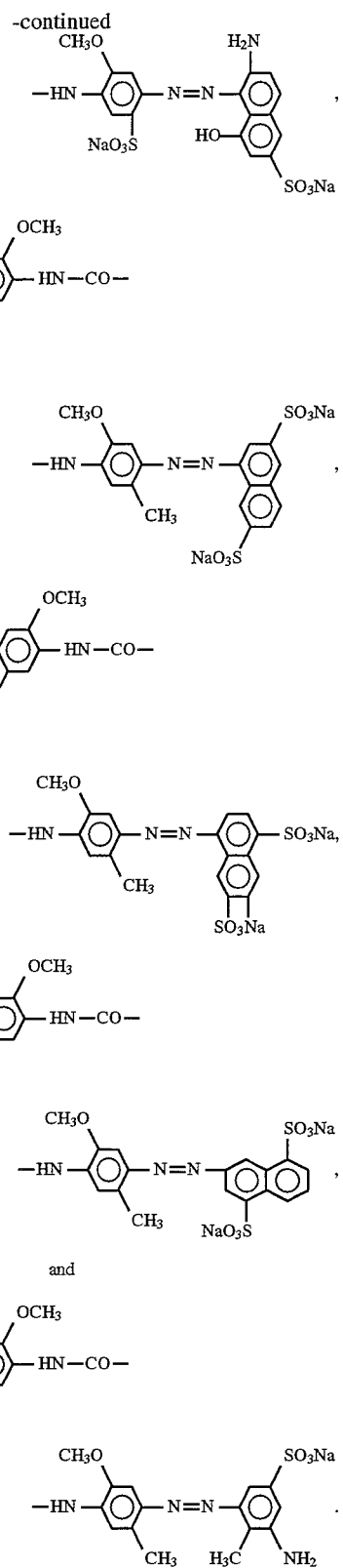
and detecting whether any of said azo dye derivative bound to said sample.
2. The method of claim 1, wherein said azo dye derivative is selected from the group consisting of

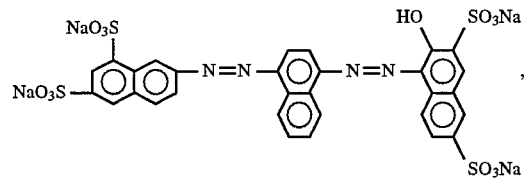
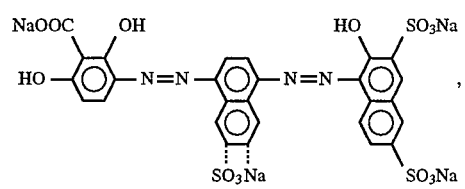
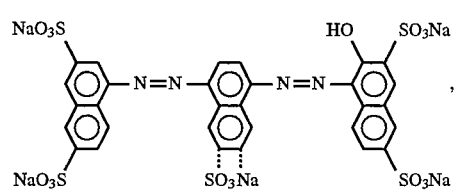
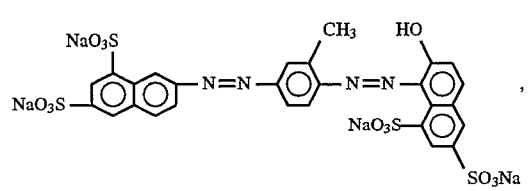
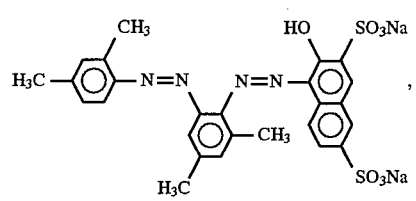
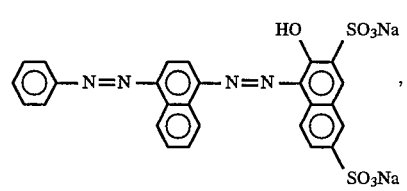
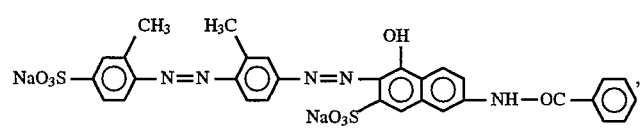
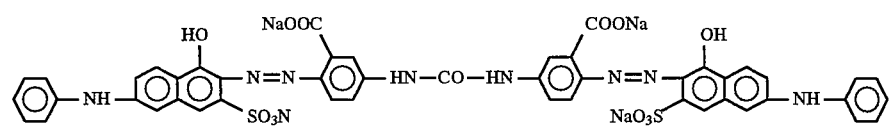
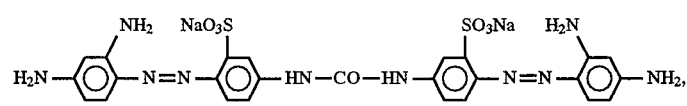
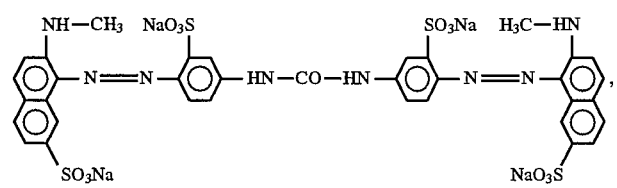

-continued
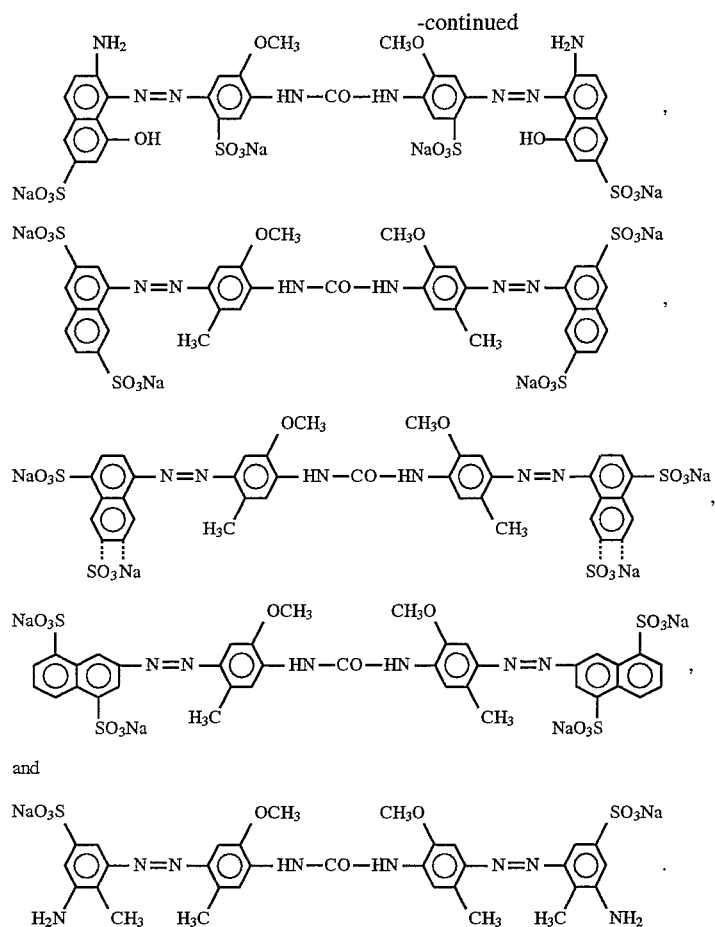
and
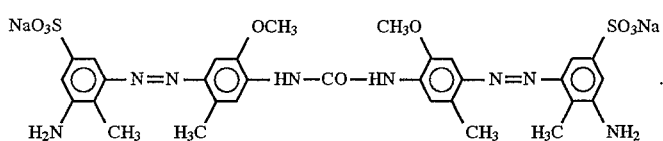
3. The method of claim 1, wherein said azo dye derivative is
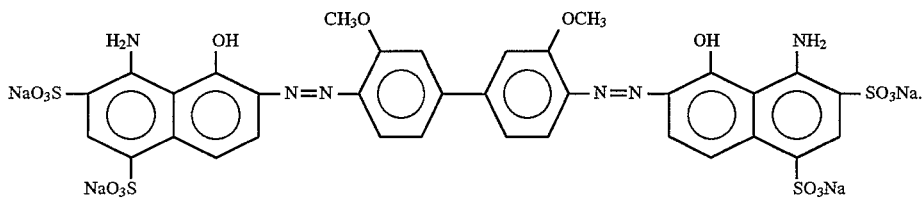
4. The method of claim 1, wherein said azo dye derivative is
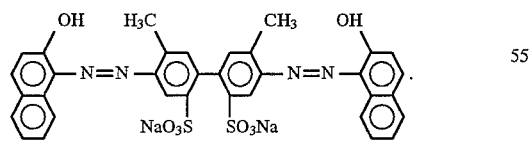

5. The method of claim 1, wherein said azo dye derivative is

[chemical structure: Ph—N=N—(naphthalene-SO₃Na)—N=N—(naphthalene-SO₃Na)—NH—Ph]

6. The method of claim 1, wherein said azo dye derivative is

[chemical structure: (2-CH₃-phenyl)—N=N—(2-CH₃-phenyl)—N=N—(naphthalene-3,6-di-SO₃Na)]

7. The method of claim 1, wherein said azo dye derivative is

[chemical structure: (NaO₃S, NaO₃S, OH-naphthalene)—N=N—(OCH₃, CH₃-phenyl)—NH—CO—HN—(OCH₃, CH₃-phenyl)—N=N—(naphthalene-OH, SO₃Na, SO₃Na)]

8. The method of claim 1, wherein said sample comprises mammalian cells.

9. The method of claim 8, wherein said mammalian cells are human cells.

10. The method of claim 9, wherein said human cells are infected with human immunodeficiency virus.

11. The method of inhibiting binding to CD4 glycoprotein comprising contacting a CD4 glycoprotein in vitro with an effective amount of an azo dye derivative selected from the group consisting of

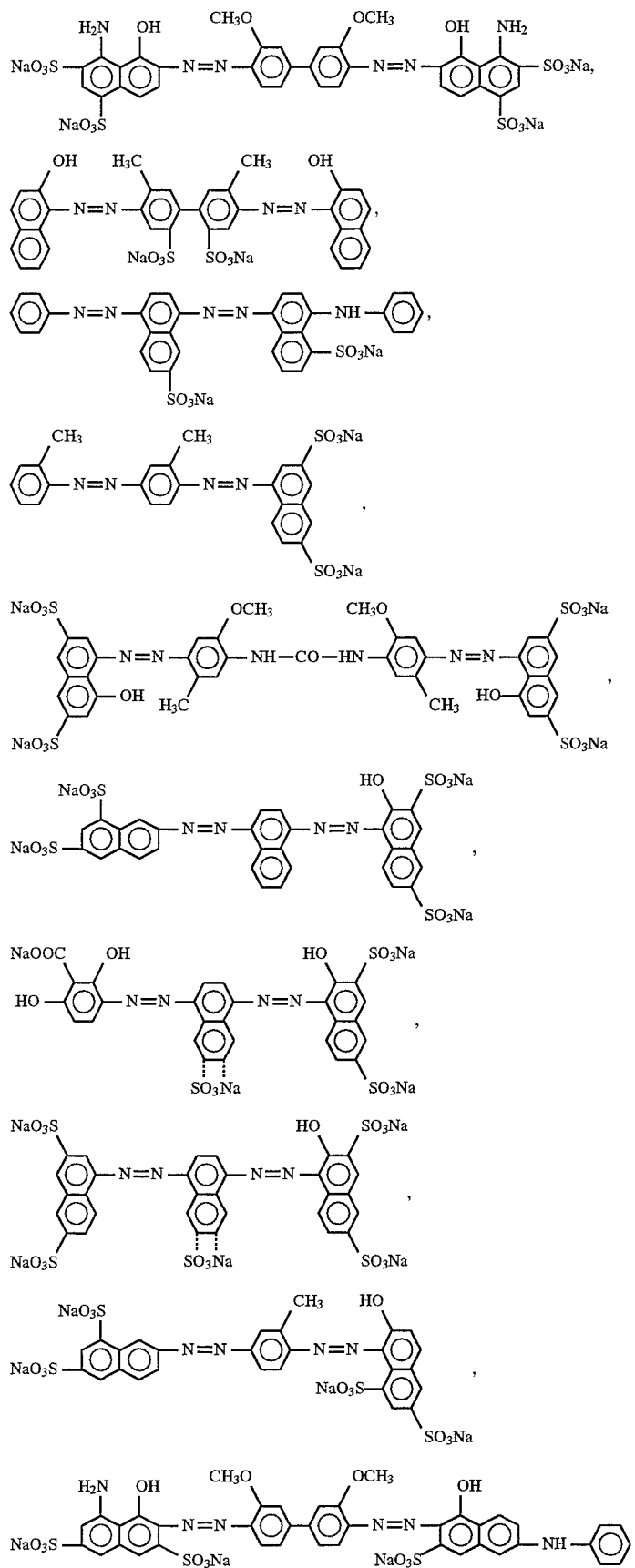

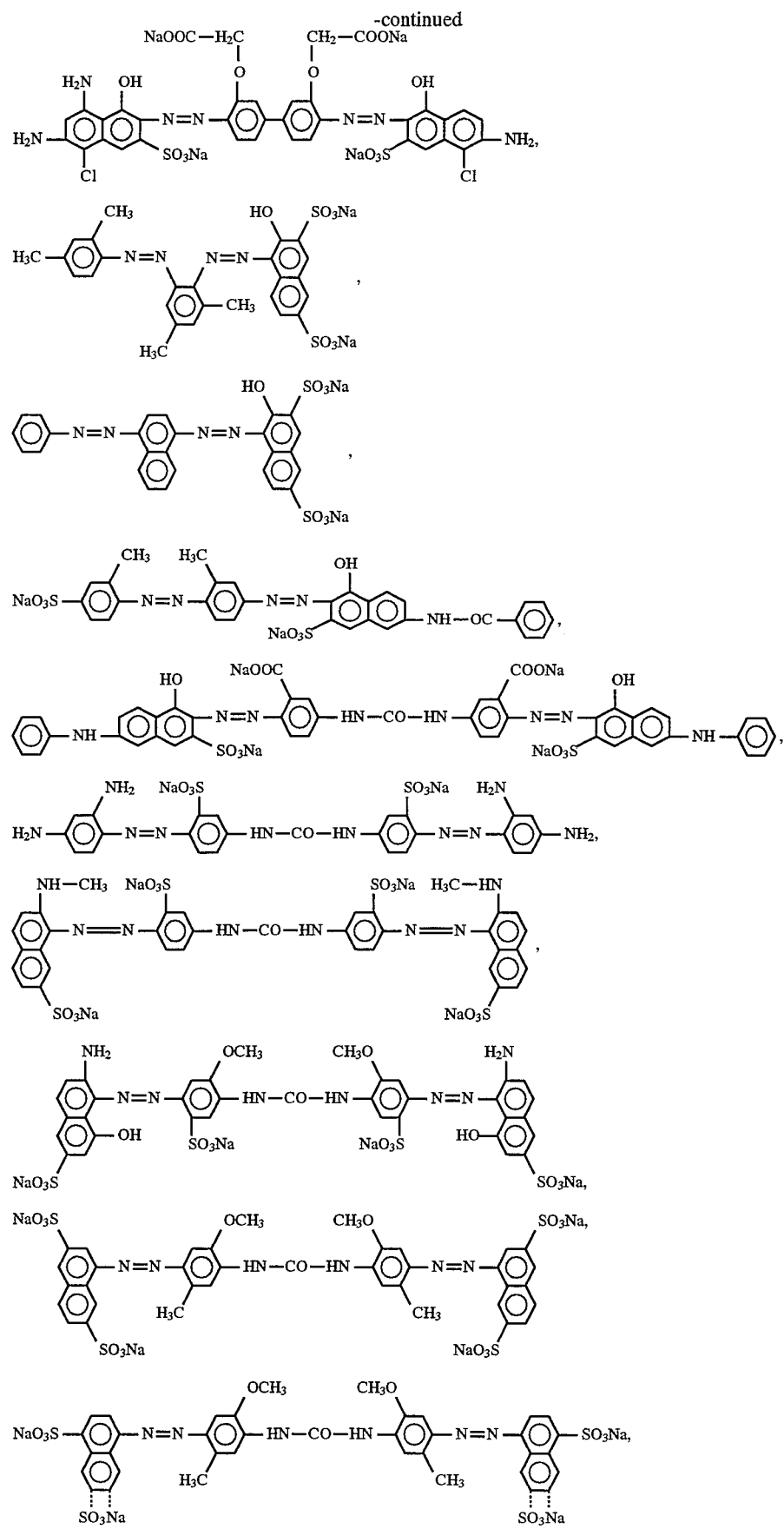

-continued
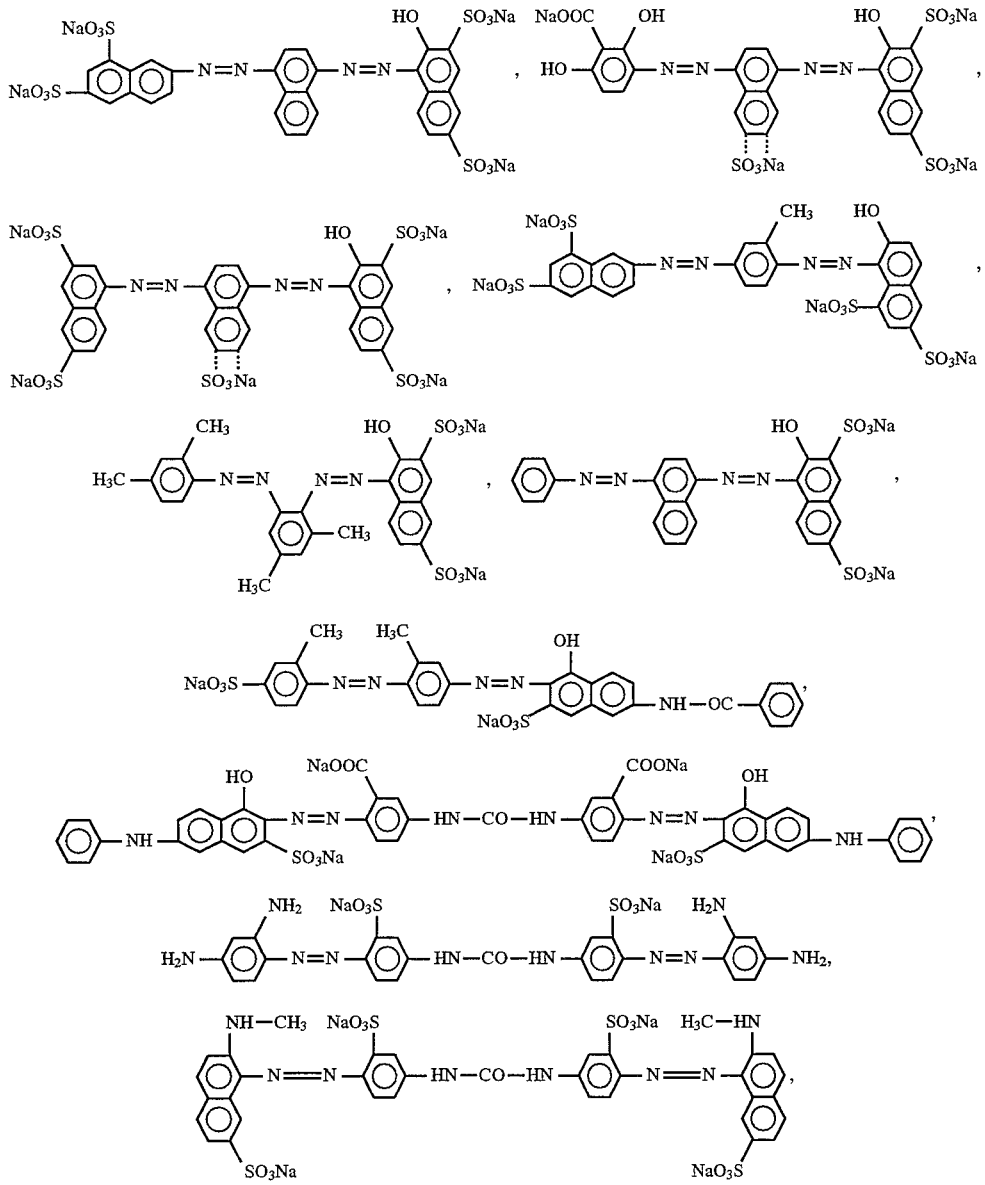
and detecting whether any of said azo dye derivative bound to said sample.
12. The method of claim 11, wherein said azo dye derivative is selected from the group consisting of

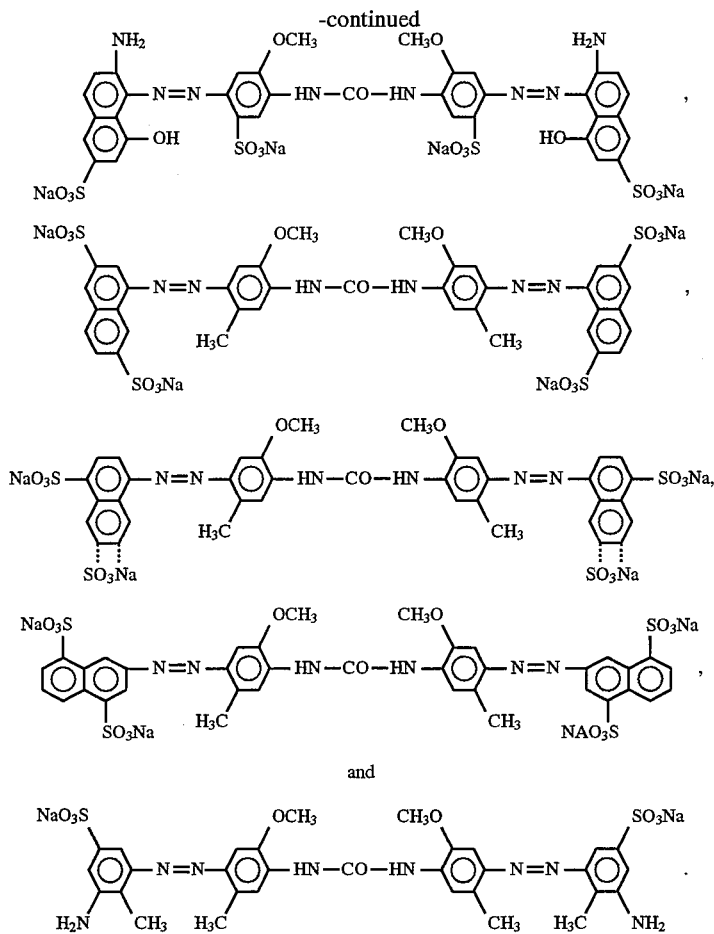
13. The method of claim 11, wherein said azo dye derivative is
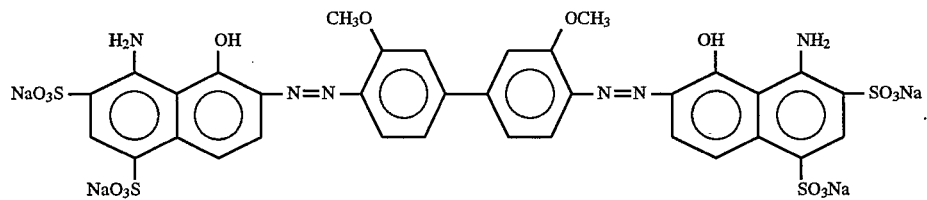
14. The method of claim 11, wherein said azo dye derivative is
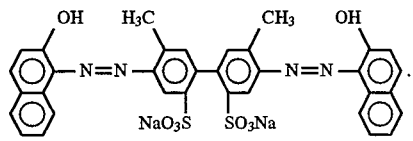

15. The method of claim 11, wherein said azo dye derivative is

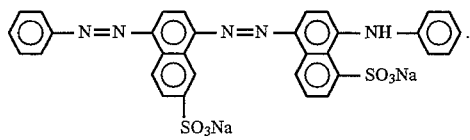

16. The method of claim 11, wherein said azo dye derivative is

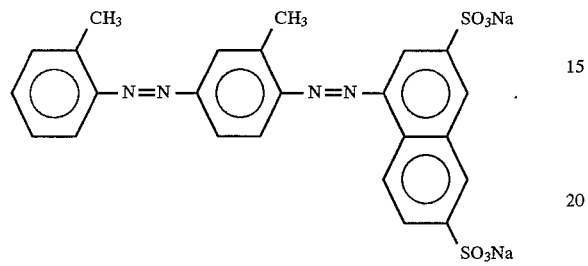

17. The method of claim 11, wherein said azo dye derivative is

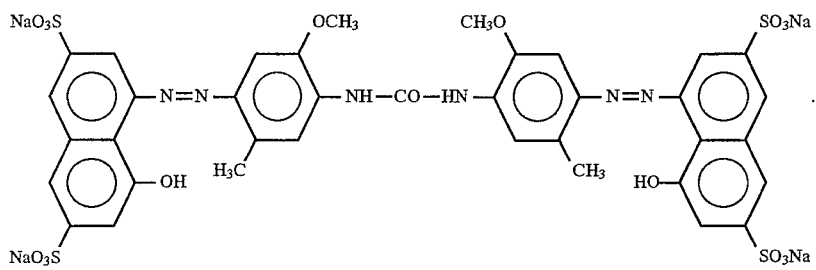

18. The method of claim 11, wherein said CD4 glycoprotein is present in a mammalian cell.

19. The method of claim 18, wherein said mammalian cell is a human cell.

20. The method of claim 19, wherein said human cell is infected with human immunodeficiency virus.

21. The method of claim 11, wherein said azo dye derivative inhibits the binding of human immunodeficiency virus to said CD4 glycoprotein.

* * * * *